United States Patent
Hare

Patent Number: 5,265,277
Date of Patent: Nov. 30, 1993

[54] ATHLETIC SHOULDER PAD COLLAR RENOVATION SYSTEM

[76] Inventor: Joseph Hare, West 1001 19th Ave., Spokane, Wash. 99203

[21] Appl. No.: 919,781

[22] Filed: Jul. 23, 1992

[51] Int. Cl.$^5$ .................................. A61F 5/02
[52] U.S. Cl. ............................... 2/45; 2/267; 2/268
[58] Field of Search ............ 2/45, 44, 2, 60, 267, 2/268; 150/160

[56] References Cited

U.S. PATENT DOCUMENTS

| | | | |
|---|---|---|---|
| 1,957,577 | 5/1934 | Chapman | 150/160 |
| 3,497,872 | 3/1970 | Mitchell | 2/2 |
| 3,514,784 | 6/1970 | McDavid | 2/2 |
| 4,135,252 | 1/1979 | Latina et al. | 2/2 |
| 4,158,242 | 6/1979 | Mithell | 2/2 |
| 4,295,227 | 10/1981 | Mitchell | 2/2 |
| 4,320,537 | 3/1982 | Mitchell | 2/2 |
| 4,322,859 | 4/1982 | Mitchell | 2/2 |
| 4,501,023 | 2/1985 | Bilberry | 2/2 |
| 4,554,681 | 11/1985 | Kirkland | 2/2 |
| 4,698,846 | 10/1987 | Wang | 2/2 |
| 4,715,066 | 12/1987 | Mitchell et al. | 2/2 |

*Primary Examiner*—Clifford D. Crowder
*Assistant Examiner*—Gloria Hale
*Attorney, Agent, or Firm*—Mark W. Hendricksen

[57] ABSTRACT

An apparatus and method to renovate collars on existing athletic shoulder pads, which can be utilized either for replacing or covering worn collars. The collar renovation system includes a uniquely shaped replacement collar cover which is stretched over and around the existing shoulder pad cover and then fastened to and around the existing shoulder pad cover.

8 Claims, 1 Drawing Sheet

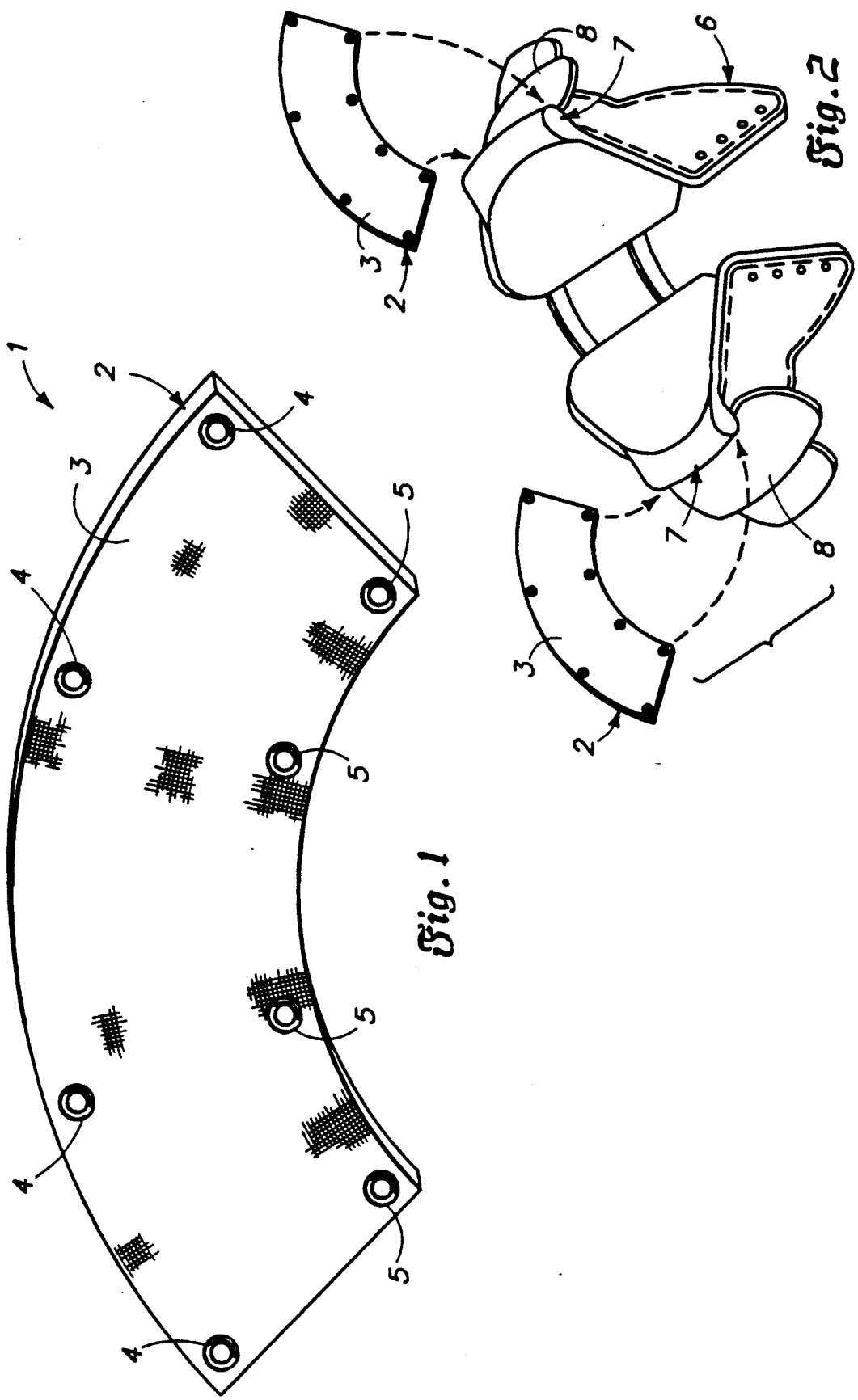

ATHLETIC SHOULDER PAD COLLAR RENOVATION SYSTEM

1. FIELD OF THE INVENTION

This invention generally pertains to a renovation system for collars on shoulder pads worn for use in athletics, with applications of the invention being, without limitation, for shoulder pads used in the games of football and hockey.

2. BACKGROUND OF THE INVENTION

While playing games requiring the use of protective wear, such as football and hockey, players utilize shoulder pads to provide protection to their shoulders, sternum and chest area. Shoulder pads provide protection through the integration of two major components: namely, an outer plastic shell and underlying padding material attached to the outer plastic shell. The outer plastic shell absorbs and redistributes forces and blows it receives, while the underlying pads absorb from the plastic shell the force and help absorb the force and distribute it over a larger surface area, thereby decreasing the risk of injury to the player.

The underlying padding material is typically attached to a plastic shell by traditional sewing methods or through the use of velcro. In the portion of the shoulder pads that surrounds a player's neck, there are generally two padded collars 7, one located on each side of the player's neck and above the shoulder area.

These padded collars are typically sewn into place on the plastic shell and a vinyl or a similar type of material is used to cover the pad material in areas where it will experience wear. The material currently used in new shoulder pads and the material currently used to cover the padded collars has the following inherent problems: The vinyl material used to cover the padding material hardens and cracks from exposure to sweat and other elements of wear; the vinyl does not have sufficient elasticity to conform well to the unusual dual curvature of the portion of the shoulder pad to which it is attached, thus creating wrinkles along the collar and which not only result in cracks and rips, but also cause the player chaffing and discomfort; there has not been a sufficiently economical or easy means to renovate shoulder pad collars.

FIG. 2 shows the replacement collar cover 1 as it is installed on an existing shoulder pad collar 7. The hard shell portion of the shoulder pad 6 is comprised of outer shell pads 8 to cover the shoulder area and collar pads 7 to protect the player's neck from the hard shell.

The currently used procedure and the resultant high cost in repairing and renovating the shoulder pads is relatively cumbersome, costly, ineffective for long term use on the shoulder pads and must be performed routinely in order to maintain the shoulder pads as usable. The typical and current method for renovating the pad and changing the collar is to:

(a) Remove the pad from the plastic shell by unstitching, typically using a razor blade;
(b) Sew a new collar over the top of the worn collar and pad;
(c) Re-sew the pad back into its original position on the plastic shell.

The forenamed procedure requires a person skilled in operating a heavy duty sewing machine capable of sewing through plastic and typically one-inch pad. The entire procedure is labor intensive, relatively expensive and should be performed by a professional.

My invention solves or greatly reduces the problems heretofore not solved by prior art or practice by providing: a shoulder pad collar renovation system which is relatively easy to install; one which can be installed by less skilled labor, such as by the school or coaching staff; one which can be installed without the need for expensive machinery and/or equipment; one which greatly reduces the amount of labor required to renovate a set of shoulder pads; and one which is relatively inexpensive.

SUMMARY OF THE INVENTION

My renovation system invention for collars on shoulder pads worn for use in athletics generally includes two elements, namely: a uniquely shaped collar cover made out of neoprene or a similar material and covered with a low friction covering such as nylon; and a means to fasten said collar cover to and around an existing shoulder pad collar pad.

It is an object of this invention to provide a replaceable collar system that is easily installed by persons who need not be skilled in sewing with heavy machinery, such as athletes or coaches, or equipment managers.

It is an object of this invention is to provide a replaceable collar system that is relatively inexpensive as compared to the current method generally used for shoulder pad renovation.

A further object of this invention to provide such a replaceable collar system that is relatively unaffected by sweat and is much more resistent to cracking than the vinyl material currently being used. This object is realized by utilization of a neoprene rubber-type or similar material, with a nylon or soft type of material covering the neoprene on the side of the replacement collar which will interact with the player's neck.

It is an object of this invention to provide a replaceable collar system that is pre-cut to form to the unusual dual curvature of a shoulder pad collar and which, when attached to said shoulder pad, is elastic enough that it does not contain wrinkles and creases. The dual curvature is the curvature: which conforms to the top of the player's shoulders, down the front and back of said shoulders; and the curvature which forms the opening for the player's necks.

It is an object of this invention to provide a replaceable collar system that is easy to attach to existing shoulder pads. One application of the fastening means of this invention features replaceable fastening rivets, which greatly eases the process of attaching the collar cover existing shoulder pad collars.

It is an object of this invention to provide a replaceable collar system that greatly reduces the labor requirements to renovate a set of shoulder pads and which therefore offers relatively inexpensive means to renovate shoulder pad collars.

Other objects, features, and advantages of this invention will appear from the specification, claims, and accompanying drawings which form a part hereof. In carrying out the object of this invention, it is to be understood that its essential features are susceptible to change in design and structural arrangement, with only one practical and preferred embodiment being illustrated in the accompanying drawings, as required.

BRIEF DESCRIPTION OF DRAWINGS

In the accompanying drawings which form a part hereof:

FIG. 1 is a top view of the shoulder pad collar pad replacement cover, showing the replacement collar and its fastener means; and FIG. 2 is a perspective view of my shoulder pad collar system, showing the replacement collar as it is to be installed on the existing collar and pad.

DESCRIPTION OF PREFERRED EMBODIMENT

My renovation system invention for collars on shoulder pads worn for use in athletics generally includes two elements, namely: a uniquely shaped collar cover made out of neoprene or a similar material and covered with a low friction covering such as nylon; and a means to fasten said collar cover to and around an existing shoulder pad collar pad.

Many of the fastening, component, material, and connection means, and other components utilized in this invention are widely known and used in the field of the invention described, and their exact nature or type is not necessary for an understanding and use of the invention by a person skilled in the art or science, and they will not therefore be discussed in significant detail.

The various components shown or described herein for any specific application of this invention can be varied or altered as anticipated by this invention. This invention comprises a unique combination of elements, each element of which can be accomplished by one of several means or variations for specific application of this invention. The practice of a specific application of any one element may already be widely known or used in the art, or by person skilled in art or science, and each will not therefore be discussed in significant detail.

FIG. 1 shows a top view of the preferred replacement collar cover 1. Although minor variations can be made to the shape, FIG. 1 shows the general preferred shape and/or configuration. The shape shown in FIG. 1 has an arcuate shape with an outer edge having a larger arc than the inner edge.

The replacement collar cover 1 can be constructed of several different types and combinations of materials within contemplation of this invention. The attributes of the material is that it needs to be semi-elastic or elastic so that it can be stretched without significant creasing and the outer surface needs to be a low friction outer layer.

The preferred material composition for the replacement collar cover 1 consists of an inner layer 2, made of a neoprene type of rubber, with a second outer surface layer 3, made of a nylon material cover attached to said inner layer 2 and acting as the outer surface of the replacement collar cover 1.

There are several different fastening means that can be utilized within the contemplation of this invention, such as rivets, sewing, staples, snaps, other fastening means, other types of stitching, velcro, etc. In the preferred embodiment, and as shown in FIG. 1, there are four nylon male attachment rivets 4 and four nylon female attachment rivets 5 to be connected to one another once the replacement collar cover 1 is in place. These rivets are self-locking.

In the preferred embodiment, the replacement collar cover 1 is a durable and flexible material, soft to the touch.

The preferred width of the replacement collar cover 1 is approximately 4 to 5 inches in width, and is approximately 12 to 14 inches in length for a small replacement collar, and approximately 14 to 16 inches in length for a larger replacement panel.

The process of attaching the replacement collar cover 1 to the existing shoulder pad collar 7 is as follows:

a. Marking a desired location on a shoulder pad for placement and attachment of the replacement collar cover;;

b. Holding the replacement collar cover 1 over the existing collar 7 and noting and marking the approximate location and position of the replacement collar cover 1 relative to the existing collar 7;

c. Mark the hole locations where the fastening means will be punched;

d. Using a hand-held punch plier, the holes must then be punched in place where they were marked;

e. The replacement collar cover 1 is then wrapped around the shoulder pad 7 and, starting at one end of the replacement collar cover 1 to the other, the male rivets 4 are fastened or attached to the female rivets 5 until the replacement collar cover 1 is placed in position.

The foregoing process should be done in a manner that pulls tight and stretches the replacement collar cover around the existing collar 7 such that it tightly encloses and fits to its new location.

While the preferred embodiment for the invention has been described in detail, those familiar with the art to which this invention relates will recognize various alternative designs and embodiments for carrying out the invention, as defined by the claims which follow.

The invention claimed is:

1. A replacement collar cover means to renovate shoulder pad collars used in athletics, comprised of:
   a. an elastic replacement collar cover means which stretches over and fastens to and around shoulder pad collars, and which has an arcuate shape with an inner edge having a smaller arc than an outer edge; and
   b. a means to fasten said replacement collar cover means to and around said shoulder pad collars, such that said replacement collar cover means is placed in a stretched condition.

2. A replacement collar cover means to renovate shoulder pad collars used in athletics as recited in claim 1, and in which the replacement collar cover means further comprises an elastic first inner layer and a second outer layer which covers said first inner layer and which interfaces with the person wearing the shoulder pads.

3. A replacement collar cover means to renovate shoulder pad collars used in athletics as recited in claim 2, and in which the first inner layer is further comprised of neoprene rubber.

4. A replacement collar cover means to renovate shoulder pad collars used in athletics as recited in claim 2, and in which the second outer covering layer which interfaces with the person wearing said shoulder pads, is further comprised of nylon.

5. A replacement collar cover means as recited in claim 1, wherein the means to fasten the replacement collar cover means to and around shoulder pad collars is comprised of three or more corresponding pairs of fastening rivets positioned near and along the radial edges of the replacement collar cover means.

6. A replacement collar cover means as recited in claim 1, wherein the means to fasten the replacement collar cover means to and around shoulder pad collars is comprised of four corresponding pairs of fastening rivets positioned near and along the radial edges of the replacement collar cover means.

7. A method of attaching a replacement collar cover means to a shoulder pad collar, comprised of the following steps:
   a. Starting with a shoulder pad used in athletics, said shoulder pad including a shoulder pad collar;
   b. Marking a desired location on said shoulder pad for placement and attachment of a replacement collar cover means;
   c. Creating holes on said shoulder pads where it is desired that fastening means be located to fasten the replacement collar cover means;
   d. Utilizing the replacement collar cover means, which has an arcuate shape with an inner edge having a smaller arc than an outer edge, stretch wrapping the replacement collar cover means around the shoulder pad collar; and
   e. Fastening the replacement collar cover means to and around the shoulder pad collar, using said fastening means in and through the holes created on said shoulder pads where it is desired that fastening means be located.

8. A method of attaching a replacement collar cover means to a collar of a shoulder pad as recited in claim 7, in which the step of fastening the replacement collar cover means to and around the shoulder pad collar is further comprised of inserting rivets in the holes created on said shoulder pad where it is desired that fastening means be located to fasten the replacement collar cover means.

* * * * *